Figure 1:
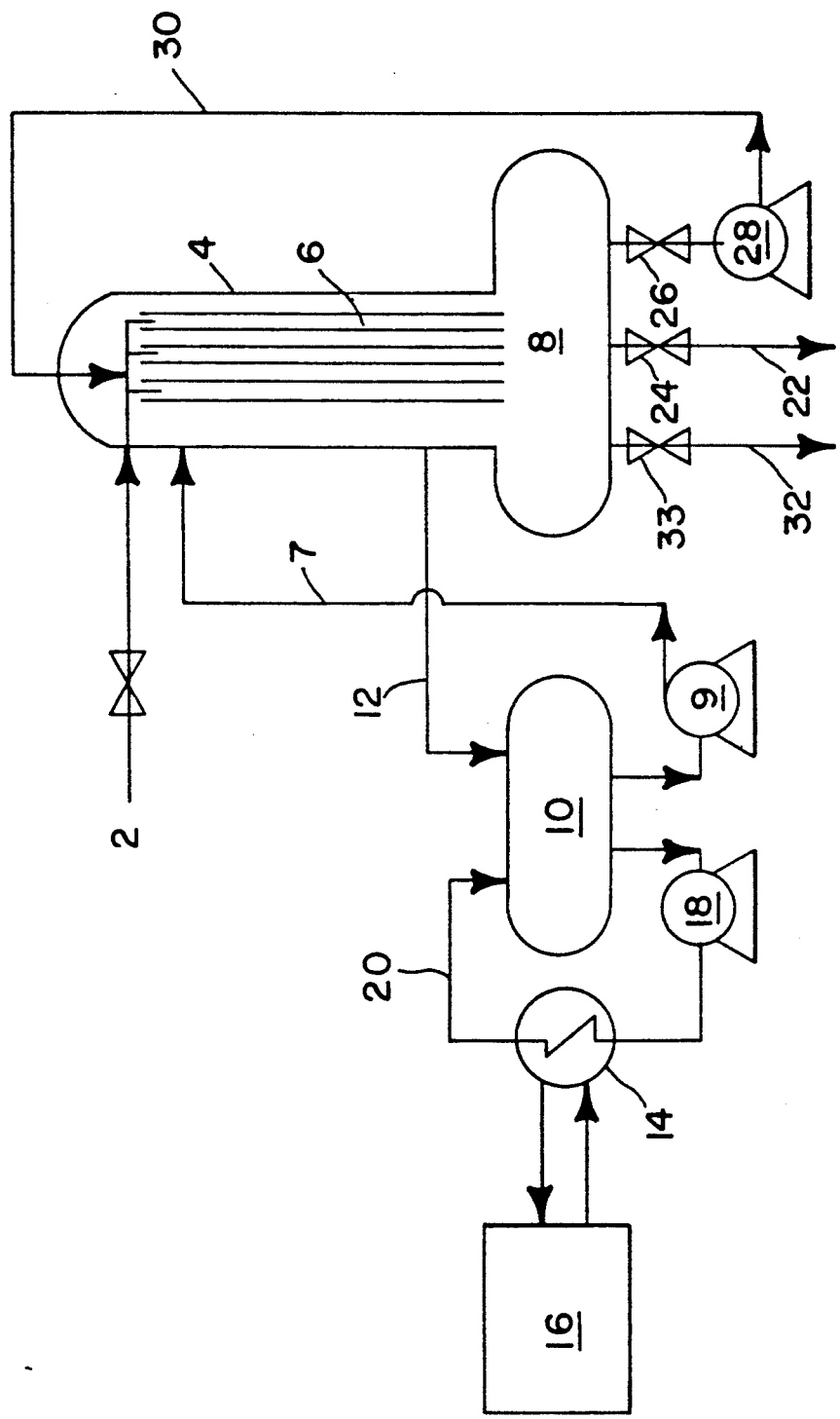
Figure 2:
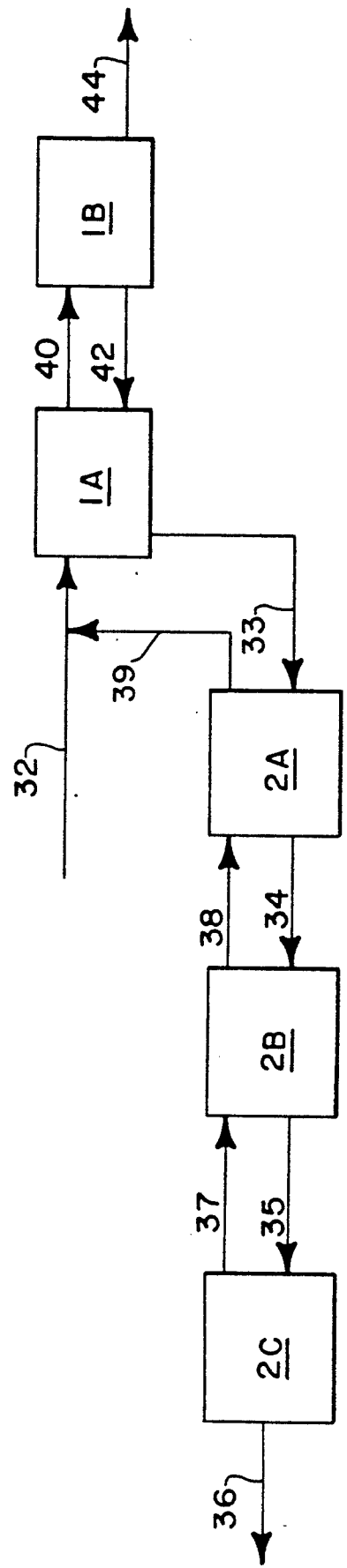

United States Patent [19]

Cohen et al.

[11] Patent Number: 5,329,021

[45] Date of Patent: Jul. 12, 1994

[54] PROCESS FOR THE PRODUCTION OF PURE VINYL PYRROLIDONE

[75] Inventors: Jeffrey M. Cohen, Fanwood; Russell B. Biss, Wayne, both of N.J.

[73] Assignee: ISP Investments Inc., Wilmington, Del.

[21] Appl. No.: 81,947

[22] Filed: Feb. 4, 1993

[51] Int. Cl.$^5$ .................................... C07D 207/267
[52] U.S. Cl. ........................................ 548/543
[58] Field of Search ................................ 548/543

[56] References Cited

U.S. PATENT DOCUMENTS 4,410,726 10/1983 Parthasarathy et al. ............ 548/543
4,873,336 10/1989 Liu et al. ............................ 548/543

*Primary Examiner*—David B. Springer
*Attorney, Agent, or Firm*—Marilyn J. Maue; Joshua J. Ward

[57] ABSTRACT

This invention relates to a process for the purification of a crude liquid N-vinylpyrrolidone product which comprises (I) product rectification by (a) subjecting said crude product containing at least 0.3 weight % of impurities to a temperature of between about 1° and 5° below the freezing point of said crude liquid to form a vinyl pyrrolidone crystalline phase and a liquid residue phase in a first crystallization step; (b) separating said liquid phase from said crystalline phase; (c) allowing said separated crystalline phase to warm gradually so as to liquify said crystals and (d) subjecting the liquified crystals of vinyl pyrrolidone to between 1 and 3 additional crystallization steps, each carried out by gradually cooling the liquified vinyl pyrrolidone to a temperature above that of the preceding crystallization step up to a temperature of 14.4° C. so as to form additional vinyl pyrrolidone crystalline and liquid residue phases with separation of vinyl pyrrolidone crystals and liquid residue phases and liquification of vinyl pyrrolidone crystals between each additional recrystallization step, recovery of N-vinyl-pyrrolidone product from the final crystallization step and (II) collecting said separated liquid residues from each crystallization step and subjecting them, sequentially, individually or collectively, to fractional crystallization in order to recover additional amounts of purified vinyl pyrrolidone product. The present process is capable of achieving up to 99.999% purity of vinyl pyrrolidone in about 98% recovery.

6 Claims, 2 Drawing Sheets

PROCESS FOR THE PRODUCTION OF PURE VINYL PYRROLIDONE

BACKGROUND OF THE INVENTION

Homopolymerized vinyl pyrrolidone has many uses in the pharmaceutical and cosmetic arts as well as in the field of copolymerization and crosslinking with various monomers for clarification of beverages. Vinyl pyrrolidone monomer, prepared by reacting acetylene with pyrrolidone or by reaction with ammonia and formaldehyde, results in a product containing from about 8 to about 0.5% impurities which are objectionable for many purposes including beverage clarification or pharmaceutical and cosmetic formulations. The current process for the preparation of vinyl pyrrolidone involves the vinylation of pyrrolidone with acetylene in the presence of a salt catalyst as described, for example, in U.S. Pat. No. 4,873,336. This process achieves a product in about 98 to 99.7% purity after recovery of product by fractional distillation. However, objectionable color and odor forming impurities, as well as polymer forming impurities, such as unreacted pyrrolidone, butene, butyne, butadiene and amine derivatives remain after distillation. These impurities in amounts above 0.5% are considered unsuitable for the above purposes; thus, product distillation is inadequate to meet the high purity requirements demanded in certain fields of application, particularly for the use of vinyl pyrrolidone polymers in medicine as plasma extenders and for cosmetics in hair fixation and other hair and skin treating applications. Requirements for beverage clarifiers are even more stringent, demanding less than a few parts per million of any taste or color altering contaminant.

Accordingly, it is an object of this invention to produce vinyl pyrrolidone in a purity of from about 99.95% to 100% by an economical and commercially feasible process.

A second object of this invention is to produce vinyl pyrrolidone in a high state of purity by a process which avoids the use of extraneous ionic chemicals as described in U.S. Pat. No. 5,039,817.

These and other objects will become apparent from the following description and disclosure.

THE INVENTION

In accordance with this invention there is provided a process which comprises subjecting a crude liquid vinyl pyrrolidone product containing an objectionable amount of impurity to product rectification in a first crystallization step by gradually cooling the crude liquid to a temperature of from 1° to 5° below its freezing point over a period of from about 20 minutes to about 1.5 hours, so as to form a solid vinyl pyrrolidone crystal phase and a liquid residue phase; separating said vinyl pyrrolidone crystals from the liquid; allowing the separated crystals to gradually warm to liquification; subjecting the liquified crystals to one or more recrystallization stages by gradually cooling to a temperature to from 1° to 5° below the freezing point of the liquified crystals which is at a temperature above the preceding crystallization step up to a temperature of 14.4° C. and repeating the separation of liquid and crystalline phases and crystal reliquification between each recrystallization step, recovering N-vinyl-pyrrolidone product from the final crystallization step and subjecting the separated liquid residue phases to product recovery by a separate series of crystallizations to recover additional product.

Generally, two crystallization stages are adequate to achieve at least 99.95% vinyl pyrrolidone purity from a crude product containing 99.4% vinyl pyrrolidone. However, at a higher impurity content, e.g. 97–98%, up to 3 recrystallization stages for the separated crystalline phases, each at an incrementally increased temperature up to 14.5° C. (the freezing point of 100% pure vinyl pyrrolidone), can be employed to achieve 99.95–100% purity. In this process, the separated liquified crystals from each recrystallization stage can be recycled to its immediately preceding crystallization stage so as to enrich the product feed thereto.

Similarly, the separated liquid phases from each vinyl pyrrolidone crystallization step can be collected and subjected, sequentially, individually or collectively, to staged crystallization-recrystallization at progressively decreasing crystallization temperatures in order to recover additional quantities of vinyl pyrrolidone entrained in the separated liquid. Because of the substantially lower vinyl pyrrolidone concentration in the separated liquid residue phase or phases, e.g. from about 70 to about 98.6%, additional stages of fractional crystallization up to 4 may be needed in the liquid residue product recovery portion of the process. The first crystallization stage of product recovery from liquid residue may require a temperature of from 10°–13° C. and the last crystallization, a temperature as low as −15° C. to crystallize the liquid residues separated from crystals of decreasing purity with subsequent melting of crystals from the liquid residues at concurrently lower temperatures. Depending on degree of purity, the vinyl pyrrolidone crystals from the final recrystallization stage in the liquid residue product recovery can be collected, liquified and directly recovered as a product of the process or, after liquification, can be recycled to a preceding crystallization stage carried out at a higher temperature. A particularly efficient method of operation for the fractional crystallization of the liquid residue involves recycling the liquified crystals obtained from each recrystallization stage in the liquid residue product recovery train to the immediately preceding crystallization stage; thus continuously enriching the feeds to the liquid residue crystallization stages and thereby raising the freezing point of said feeds undergoing crystallization so as to allow recovery of entrained vinyl pyrrolidone from the liquid phases at higher, more economical temperatures than would be effective without recycling.

In the present process, it is recommended, but not essential, that the warming of crystals separated at each stage of the process be conducted by gradually raising the temperature to permit maximum liquid separation of impurities from the crystals. The purified vinyl pyrrolidone crystals obtained from the final crystallization of the separated vinyl pyrrolidone crystals are allowed to warm to ambient temperature and the resulting liquid product stabilized with less than 1 wt. % of a base, such as for example ammonia, tenamine (N,N-di-sec-butyl-p-phenylene diamine), sodium hydroxide, and the like.

Generally, the freezing point at which crystallization occurs varies inversely with the concentration of impurities contaminating the vinyl pyrrolidone. By way of illustration, for the crystallization of a crude vinyl pyrrolidone containing about 0.3% impurity, the contaminated vinyl pyrrolidone is cooled to between about 13.5° and about 14° C.; at 0.5% impurity, the vinyl pyrrolidone is crystallized at about 12°-13° C. and at 30% impurity, the vinyl pyrrolidone is crystallized at a temperature of about −5° C. Cooling below the freezing point of the contaminated vinyl pyrrolidone liquid is effected by a gradual reduction of temperature since flash freezing or shock chilling does not permit the slow growth of crystals which is needed to minimize inclusion of residue contaminants. Any conventional cooling media which is capable of remaining liquid at the required temperature, e.g. 10°-20° below the freezing point of the vinyl pyrrolidone material undergoing crystallization is suitably employed in indirect heat exchange for this invention. Such media include glycol/water or alcohol/water mixtures as well as thermal oils. However, direct refrigeration under controlled gradual cooling conditions can also be employed. Generally, a cooling rate of between about 0.1° and 1°/min. is recommended for vinyl pyrrolidone rich feeds; although a rate of up to about 5°/min. can be tolerated for vinyl pyrrolidone lean feeds.

Separation of the vinyl pyrrolidone crystals and liquid residue at each crystallization stage can be effected by simple decantation or drainage; although other conventional means, such as vacuum fitration, etc. can be employed if desired.

The crude feed to the present process can be obtained from many sources for the synthesis of N-vinyl-pyrrolidone. For example, the synthesis can be effected by the reaction of 2-pyrrolidone with acetylene introduced at a partial pressure of from 25-125 psig in the presence of an alkali metal oxide catalyst in a nitrogen purged reactor and effecting vinylation at about 125° to about 185° C. until at least 50% conversion is obtained; removing a major portion of unreacted pyrrolidone by fractional distillation and recovering crude vinyl pyrrolidone product while recycling unreacted pyrrolidone to the reactor. The crude vinyl pyrrolidone containing from about 4 to about 0.6% impurity thus obtained is subjected to the crystallization process of this invention as described for FIGS. I and II which illustrate a typical operation.

FIG. I is a flow diagram describing the rectification of the crude vinyl pyrrolidone product containing 0.6% impurities, obtained by the aforedescribed vinylation reaction. FIG. II represents a block flow diagram describing the vinyl pyrrolidone crystal rectification with simultaneous product recovery from separated liquid residue phases of the process.

In FIG. I, 2920 lbs. of 98.2% crude vinyl pyrrolidone (VP) is fed by line 2 into Sulzer MWB crystallizer 4 which is equipped with sump 8 and a plurality of crystallization tubes 6 over which thermal oil is constantly circulated by entering crystallizer 4 via line 7 from a temperature control system hereinafter described and exiting from crystallizer 4 via line 12 for recycle to temperature control. The temperature control system, which provides means for intermittent cooling of the oil during crystallization of crude vinyl pyrrolidone and gradual warming of the oil after recovery of the crystals from the liquid residue, comprises refrigeration unit 16, equipped with indirect heat exchanger 14, thermal oil reservoir 10 from which oil is withdrawn in line 20 and pumped via pump 18 through heat exchanger 14 a before being returned to reservoir 10 and then pumped by pump 9 to crystallizer 4 through line 7.

During the initial crystallization stage, valves 26 and 33 are closed and valve 24 is opened. The oil entering 4, which is initially cooled to about 5° C., passes over tubes 6 while vinyl pyrrolidone introduced into tubes 6 gradually forms crystals on the inner walls of the tubes over a period of 60 minutes and a liquid residue containing entrained VP and contaminants is separated from the crystals by draining into sump 8 after which the residue is withdrawn by open valved line 22 as a by-product or treated for further recovery of VP product as described in FIG. II. After removal of the liquid residue, valve 24 is closed, valve 26 is opened and the temperature of the oil controlled by unit 16 is gradually raised in crystallizer 4 over a period of 40 minutes to 20° C. whereupon the separated crystals are liquified to form a melt and 1980 lbs. of 99.5% vinyl pyrrolidone melt drains into sump 8 from which it is recycled to the top of crystallizer 4 and into tubes 6 by means of pump 28 and valved line 30 to enrich the feed to crystallizer 4.

The temperature of the oil passed over tubes 6 is then adjusted to 10° C. whereupon crystals from the vinyl pyrrolidone enriched liquid melt are again formed on the inner walls of tubes 6 and a second liquid residue is formed and separated from the reformed crystals, passed to sump 8 and withdrawn in line 22 by opening valve 24.

After withdrawal of the residue, valve 24 is closed and the temperature of the oil is then raised to 20° C. to liquify the crystals and 1622 lbs. of the liquid melt are collected in sump 8 to provide liquid vinyl pyrrolidone at a purity of 99.999%, which is recovered as the product of the process from open valved line 32.

Many modifications and variations in the above process will become apparent from this disclosure. For example, where the concentration of VP in the crude feed entering the crystallizer from line 2 is less than 98%, it can be subjected to additional processing recycles via line 30 including crystallization, residue separation, crystal liquification and recycle to crystallizer 4 from sump 8, before the desired product purity is achieved. Also, the crystallizer can be designed so that the thermal oil is passed through tubes 6 and the VP feed and recycled melt is passed over tubes 6 for crystal formation on the outer walls of the tubes.

FIG. II provides a more detailed description of VP recovery from the separated liquid residue phase or phases.

In FIG. II, 3020 lbs. of 99.4% vinylpyrrolidone liquid in line 32 is introduced to first crystallization zone 1A wherein the liquid is gradually cooled to 11.5° C. over a period of 70 minutes during which first crystalline and first liquid residue phases are formed. The first liquid residue phase containing 98.6% vinyl pyrrolidone is separated from the crystals and is passed to second crystallization zone 2A by means of line 33 wherein 550 lbs. of the liquid separated in zone 1A, together with a supplementary VP feed, hereinafter explained, is gradually cooled to 9.5° C. over a period of about 60 minutes during which second crystalline and second liquid residue phases are formed and separated. The second liquid residue phase (145 lbs.) containing 94% vinyl pyrrolidone is passed to third crystallization zone 2B via line 34 wherein this liquid together with a supplementary VP feed is gradually cooled to 3.5° C. over a period of 90 minutes during which third crystalline and third liquid phases are formed. The third liquid residue phase from zone 2B (32 lbs) containing 82% vinyl pyrrolidone is separated from the third crystalline phase and is then passed to crystallization zone 2C via line 5 wherein this liquid is gradually cooled to −3° C. over a period of 90 minutes during which a final fourth crystalline and fourth liquid residue phases are formed. The fourth liquid residue phase (12 lbs) containing 70% vinyl pyrrolidone is separated from the fourth crystalline phase and is withdrawn from the process through line 36.

In crystallization zones (2A-2C) each of the crystalline phases is gradually warmed to liquification temperature after the removal of liquid residue and the resulting melt is passed as the supplementary feed to the immediately preceding crystallization zone through lines 37-39 as shown. The crystalline melt temperature in zone 2A is about 10.5° C.; in 2B about 5° C. and in 2C about −2° C. for optimum performance.

In crystallization zone 1A, after the separation and removal of the first liquid residue phase, the remaining crystalline content is melted at 12° C. over a period of 25 minutes and the resulting melt (2490 lbs) containing 99.6% vinyl pyrrolidone is passed by means of line 40 to a fifth crystallization zone 1B wherein the melt is cooled to 14° C. over a period of 50 minutes during which a fifth crystalline phase of 99.95% vinyl pyrrolidone is formed and separated from a fifth liquid residue phase containing 595 lbs. of 99.6% vinyl pyrrolidone. The fifth liquid residue phase is passed to the first crystallization zone 1A through line 42 as supplementary feed thereto, after which the remaining 99.95% vinyl pyrrolidone crystals in the fifth crystallization zone 1B are allowed to warm to room temperature and then removed from zone 1B via line 44 as the product of the process.

Higher N-vinylpyrrolidone purity, up to 99.99%, is achieved by passing the fifth liquid residue phase to zone 2A in place of 1A, melting the remaining fifth crystalline phase followed by repetative recycle of the crystal melt from zone 1B to 1A before finally recovering product in line 44.

The present process provides an economical, commercially feasible method for achieving pure, stable vinyl pyrrolidone by a treatment of improved efficiency and without loss of highly reactive vinyl pyrrolidone product to polymer which is unavoidable with repeated distillations over long periods at higher temperatures. Further, the present process succeeds in removing both polar and non-polar impurities in a single operation at reduced cost. Additionally, this process can be carried out in a batch or continuous operation; the later being effected, for example, by alternating pairs of crystallization and recrystallization chambers operated in tandem or in a single crystallizer unit having means for liquid drainage, intermittent warming and recycle of separated liquified crystals.

What is claimed is:

1. A process for purifying N-vinylpyrrolidone which comprises: rectifying a first crude N-vinylpyrrolidone solution by gradually reducing the temperature of the solution to between about 1° and about 5° below its freezing point in a first crystallization zone so as to form a solid N-vinyl-pyrrolidone crystalline phase and a liquid residue phase; separating said liquid residue phase from said crystalline phase; gradually warming the separated crystals to form a liquid melt having a higher N-vinyl-pyrrolidone concentration than said first crude solution and subjecting said liquid melt to from 1 to 3 additional recrystallization stages by gradually cooling the melted crystals from each stage to a temperature of from 1° to 5° below its freezing point and repeating the above separation of crystalline and liquid residue phases followed by warming of the separated crystals between each crystallization stage to form a melt and recovering N-vinylpyrrolidone melt from the final crystallization stage as the product of the process.

2. The process of claim 1 wherein the liquid residue phase separated from the first crystallization zone is recovered and is separately cooled to a temperature of from about 1° to about 5° below its freezing point to form an additional N-vinylpyrrolidone crystalline phase and an additional liquid residue phase, the resulting phases are separated, and the resulting separated crystals are warmed to liquification to form a melt.

3. The process of claim 2 wherein the melt from the crystals separated from crystallization of the liquid residue is recovered as a product of the process, 4. The process of claim 2 wherein the melt from the crystals separated from crystallization of the liquid residue is introduced to the first crystallization zone as supplementary feed thereto, 5. The process of claim 1 wherein the liquid residue phase separated from the first crystallization zone is recovered and is separately subjected to a series of recrystallization steps each of which is effected at a progressively lower temperature to form additional N-vinylpyrrolidone crystalline phases and liquid residue phases, which phases are separated in each crystallization step; the separated liquid residue from each crystallization step before the final step is fed to the immediately succeeding crystallization step and the N-vinylpyrrolidone crystals separated in each crystallization step are separately warmed to liquification and then passed as supplementary feed to the crystallization step immediately preceding.

6. The process of claim 5 wherein the liquid residue phase recovered from the first crystallization zone is subjected from 1 to 4 recrystallization steps.

* * * * *